(12) United States Patent
Noordover et al.

(10) Patent No.: US 9,341,611 B2
(45) Date of Patent: May 17, 2016

(54) GREASE TEST KIT AND METHODS OF TESTING GREASE

(75) Inventors: Alain Noordover, Utrecht (NL); Sebastien David, Ouderkerk a/d Amstel (NL); Frank Fiddelaers, Gorinchem (NL); Albert van den Kommer, Nieuwegein (NL)

(73) Assignee: AKTIEBOLAGET SKF, Goteborg (SE)

( * ) Notice: Subject to any disclaimer, the term of this patent is extended or adjusted under 35 U.S.C. 154(b) by 874 days.

(21) Appl. No.: 13/511,703

(22) PCT Filed: Nov. 24, 2010

(86) PCT No.: PCT/US2010/058095
§ 371 (c)(1),
(2), (4) Date: Sep. 21, 2012

(87) PCT Pub. No.: WO2011/066455
PCT Pub. Date: Jun. 3, 2011

(65) Prior Publication Data
US 2013/0152674 A1    Jun. 20, 2013

Related U.S. Application Data

(60) Provisional application No. 61/281,974, filed on Nov. 25, 2009.

(51) Int. Cl.
| | |
|---|---|
| *G01N 33/26* | (2006.01) |
| *G01N 11/02* | (2006.01) |
| *G01N 3/08* | (2006.01) |
| *G01N 11/00* | (2006.01) |
| *G01N 33/30* | (2006.01) |
| *G01N 33/28* | (2006.01) |

(52) U.S. Cl.
CPC .................. *G01N 33/26* (2013.01); *G01N 3/08* (2013.01); *G01N 11/00* (2013.01); *G01N 11/02* (2013.01); *G01N 33/2888* (2013.01); *G01N 33/30* (2013.01); *G01N 2203/0222* (2013.01)

(58) Field of Classification Search
CPC ........ G01N 11/02; G01N 11/04; G01N 33/26
See application file for complete search history.

(56) References Cited

U.S. PATENT DOCUMENTS

| | | | | |
|---|---|---|---|---|
| 2,104,163 | A | * | 1/1938 | McJunkin .................. 73/54.28 |
| 2,385,656 | A | * | 9/1945 | Smith .............................. 73/10 |

(Continued)

FOREIGN PATENT DOCUMENTS

| | | | | |
|---|---|---|---|---|
| JP | | 58055838 A | * | 4/1983 |
| SU | | 455272 A | * | 4/1975 |

OTHER PUBLICATIONS

Garg, Alka et al., "Spreading of Semisolid Formulations" Pharmaceutical Technology, Sep. 2002.*

*Primary Examiner* — Paul West
(74) *Attorney, Agent, or Firm* — Inventa Capital PLC

(57) ABSTRACT

A kit for testing grease includes components for testing consistency, oil bleed characteristic and contamination. Consistency of the grease is tested by compressing a sample of the grease between two surfaces (e.g., glass plates), measuring the extent of spread, and comparing the measured spread to a calibrated reference. Oil bleed characteristic is tested by placing a quantity of the used grease on a test medium, heating the test sample, measuring a dimension of the grease quantity on the heated test sample, and determining the bleed characteristic of the used grease by comparing the dimension of the grease quantity to a reference. A contamination test may be performed by further compressing the consistency sample and inspecting the sample both by the naked eye and with a microscope.

17 Claims, 14 Drawing Sheets

(56) References Cited

U.S. PATENT DOCUMENTS

| | | | |
|---|---|---|---|
| 5,433,872 A * | 7/1995 | Brauer et al. ................ 508/136 |
| 6,598,464 B1 | 7/2003 | Rossi | |
| 6,840,082 B2 | 1/2005 | Evans | |
| 2005/0245406 A1 | 11/2005 | Scherer et al. | |

\* cited by examiner

| NLGI Grade | Cone penetration (0.1 mm) |
|---|---|
| 000 | 445-475 |
| 00 | 400-430 |
| 0 | 355-385 |
| 1 | 310-340 |
| 2 | 265-295 |
| 3 | 220-250 |
| 4 | 175-205 |
| 5 | 130-160 |
| 6 | 85-115 |

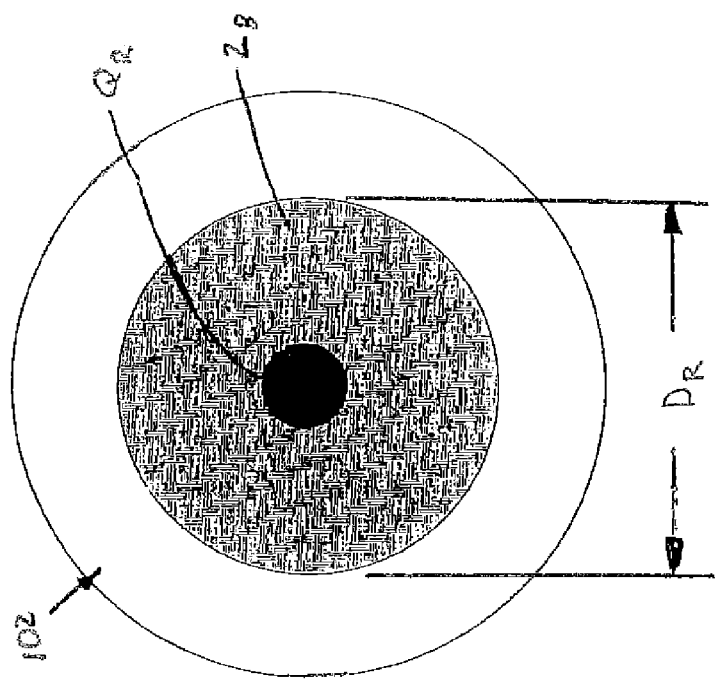
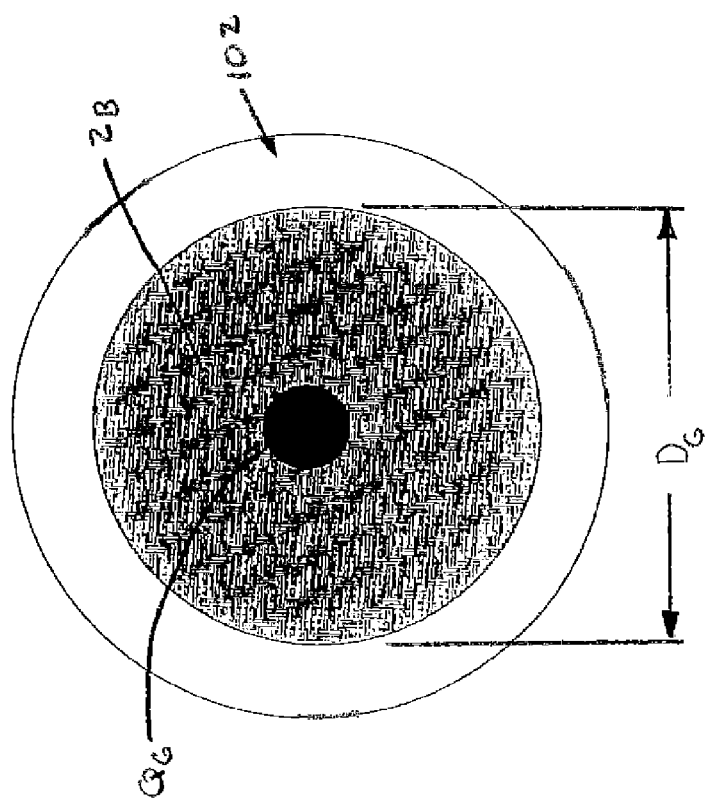
FIG. 20

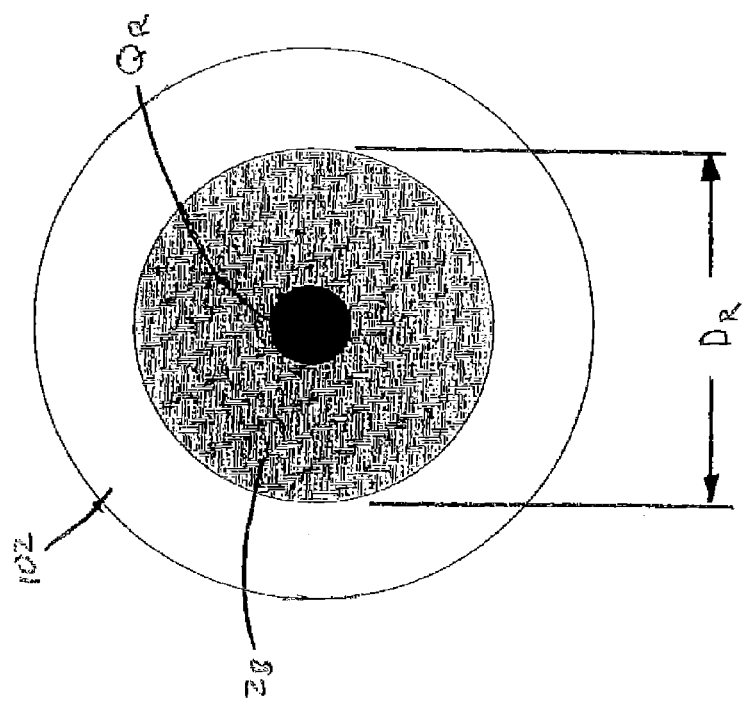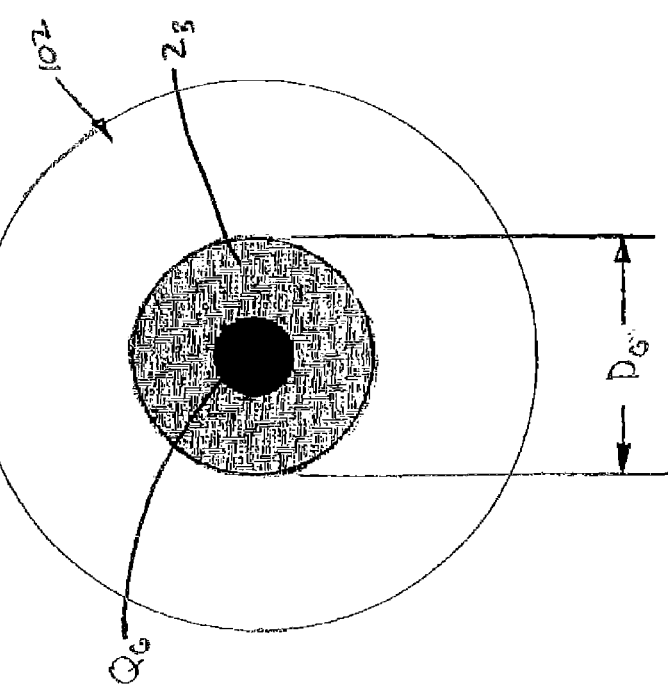
FIG. 121

GREASE TEST KIT AND METHODS OF TESTING GREASE

This non-provisional patent application Ser. No. 13/511,303 filed on Sep. 21, 2012 claims priority to PCT application serial number PCT/US10/58095 filed on Nov. 24, 2010, which claims benefit of U.S. Provisional application Ser. No. 61/281,974 filed on Nov. 25, 2009.

The present invention relates to material testing, and more particularly to devices and methods for testing the properties of grease used in machine lubrication.

Greases are used in a variety of engineering applications to lubricate moving machine surfaces. A grease is defined as a solid to semi-fluid product of a dispersion of a thickening agent in a liquid lubricant, where other ingredients imparting special properties may be present. A grease typically comprises a lubricating oil, a thickener substance and additives. Due to its nature, a grease possesses a yield stress value, which corresponds to the shear stress that has to be applied on the grease for it to start moving. Once this yield stress value has been exceeded, a grease then exhibits shear-thinning rheological properties, which means that the apparent viscosity of the grease reduces under shear.

The interactions of the lubricating oil, additives and the thickener are important in determining the properties of the grease in terms of lifetime or lubricating properties. The thickness, or stiffness, of a grease is a measure of its consistency and relates to its ability to remain in place. Owing to the multi-phase nature of greases, the stiffness does not correspond simply to viscosity.

For modern greases, the consistency is classified according to a scale developed by the National Lubricating Grease Institute (NLGI). If the grease is too stiff (high NLGI number), then an engineering component, such as a bearing, may become starved of lubricant, increasing frictional contact and wear between the parts and reducing component lifetime. On the other hand, if the grease is too soft (low NLGI number), then leakage can occur. This also reduces the component lifetime.

Depending on the operating conditions, certain greases tend to harden or soften in use and this can interfere with equipment function. For this reason, maintenance procedures typically specify the hardness of a grease and dictate when the grease should be replaced. Measurement of consistency during service can give information about the state of the grease. For example, a decrease in consistency may mean that grease has degraded because of intense shearing, ingress of water, etc. On the other hand, an increase in consistency may mean that the grease has lost base oil or indicates the ingress of solid contamination.

The NLGI defines grease consistency grades based on the ASTM D217 worked penetrations standard. The softest grade, which is fluid, is "000", while the stiffest grade is "6".

Determination of the NLGI grade of a grease requires very specialist equipment. The standard test, as defined in ASTM D217, uses a penetrometer and is based on the degree of penetration achieved by allowing a standardized cone to sink into the grease at a temperature of 25° C. for a period of five seconds. The depth of penetration is measured on a scale with a 0.1 mm resolution. Obviously, softer greases allow the cone to penetrate further into the grease than stiffer greases.

The complexity and size of the standard ASTM D217 test equipment means that it is not suitable for measuring grease consistency on-site and away from the laboratory. Instead, an on-site test has been developed which involves collecting a series of greases of known grades and then comparing these to the grease from the engineering component in question, for example a bearing. A knife or spatula is used to work the greases whereby a subjective view is arrived at regarding the relative consistency of the bearing grease to the known grades. In a similar manner it is possible to perform a direct comparison between a new sample and a sample taken from a bearing. These tests suffer from lack of reproducibility between different operators and poor accuracy. The tests are also time-consuming.

The present invention aims to address at least some of the problems associated with the prior art.

SUMMARY OF THE INVENTION

In one aspect, the present invention provides a method for determining the consistency of a grease. The method comprises the steps of:

(1) compressing a volume of grease between two surfaces by applying a compressive force to the surfaces for a period of time, such that the grease is caused to spread between the surfaces;

(2) measuring an extent that the grease has spread under compression;

(3) determining grease consistency from the measured extent of grease spreading, on the basis of a relationship therewith.

In one embodiment of the inventive method, the grease consistency determined corresponds to a penetration depth according to ASTM D217. In another embodiment, the grease consistency determined corresponds to a NLGI grade. The inventor has found that there is a direct correlation between how much a predetermined volume of grease spreads under the application of a predetermined compressive force and how far a standardized cone penetrates into the same grease. Given that NLGI grades are based on cone penetration depths, there is also a direct correlation with the NLGI grades.

Consequently, a relationship can be derived between grease spreading under compression and grease consistency, whereby the relationship is calibrated with respect to:

(i) the volume of grease compressed,
(ii) the compressive force applied, and
(iii) the period of time that the compressive force is applied.

The calibrated relationship can be used as a formula, whereby the measured extent of grease spreading under compression is the input variable. Similarly, the calibrated relationship may be used to create a lookup table of grease consistency values that correspond to measured extent of spreading. In an advantageous further development, the calibrated relationship is used to create a scale having graduated markings, whereby a distance between the graduated markings corresponds to an extent of grease spreading under compression and the graduated markings correspond to a grease consistency—i.e. a cone penetration depth or a (part number of a) NLGI grade. The advantage of this further development is that the scale can be used to measure the extent of spreading and provides an immediate indication of the grease consistency.

Temperature also has an effect on grease consistency, although the extent to which grease consistency is influenced by temperature is very dependent on the type of grease and its chemistry. Thus, in a further development of the method, the relationship used in the step of determining is further calibrated with respect to a predetermined temperature range. The temperature range may span an interval of 50° C. for greases that are insensitive to temperature. Preferably, the temperature range spans an interval of 20° C. or less. More preferably, the temperature range spans an interval of less than 10° C., which enables grease consistency to be determined for a wide range of grease. If a grease to be tested is particularly sensitive to temperature and an extremely accurate determination is required, the relationship used to determine grease consistency is preferably calibrated with respect to a specific temperature. Consequently, the method according to the invention may comprise a step of measuring the temperature of the grease or measuring the ambient temperature at which the method is performed.

In another aspect, the present invention provides a grease testing apparatus for performing the above method. The apparatus comprises:

(a) first and second surfaces;
(b) means for applying a volume of grease to one of the surfaces;
(c) means for applying a compressive force to the first and second surfaces, so that, in use, the volume of grease is caused to spread between the surfaces;
(d) means for measuring the extent of grease spreading under compression; and
(e) means for determining the consistency of the grease using a relationship between grease consistency and the extent of spreading under compression, where the relationship is calibrated with respect to:
 (i) the volume of grease compressed,
 (ii) the compressive force applied,
 (iii) the period of time that the force is applied, and preferably also
 (iv) a predetermined temperature or temperature range.

In a further aspect, the present invention provides a calibrated scale for use in determining the consistency of a grease. The scale comprises a graduated set of markings that are calibrated to correspond to cone penetration depths according to ASTM D217 or to grease classification grades. The scale is configured to allow visual determination of the grease consistency by observing the extent of spreading exhibited by a predetermined volume of grease placed centrally to the markings that has been subjected to compression by a predetermined force for a predetermined period of time. In a preferred embodiment, the graduated markings on the scale are concentric, circular markings. The scale is calibrated with respect to the predetermined volume of grease, the predetermined compressive force, the predetermined period of time and preferably also a predetermined temperature or temperature range.

In yet another aspect, the present invention is a method for determining a bleed characteristic of used grease. The method comprises the steps of: forming a test sample by placing a quantity of the used grease on a test medium; heating the test sample; measuring a dimension of the grease quantity on the heated test sample; and determining the bleed characteristic of the used grease by comparing the dimension of the grease quantity to a reference.

In an even further aspect, the present invention is a kit for testing the bleed characteristic of used grease. The kit comprises at least one piece of a test medium configured to receive a quantity of the used grease so as to form a test sample and a heater configured to heat the test sample. A scale is provided for measuring a dimension of the used grease on the test sample after the step of heating the sample.

BRIEF DESCRIPTION OF THE SEVERAL VIEWS OF THE DRAWINGS

The present invention will now be described further with reference to the accompanying drawings, provided by way of example, in which:

FIG. 20 is a plan view of a comparison between a test sample and reference sample, depicting an increased bleed characteristic of the used grease;

FIG. 21 is a plan view of a comparison between a test sample and reference sample, depicting an decreased bleed characteristic of the used grease.

DETAILED DESCRIPTION OF THE INVENTION

Figure 1:
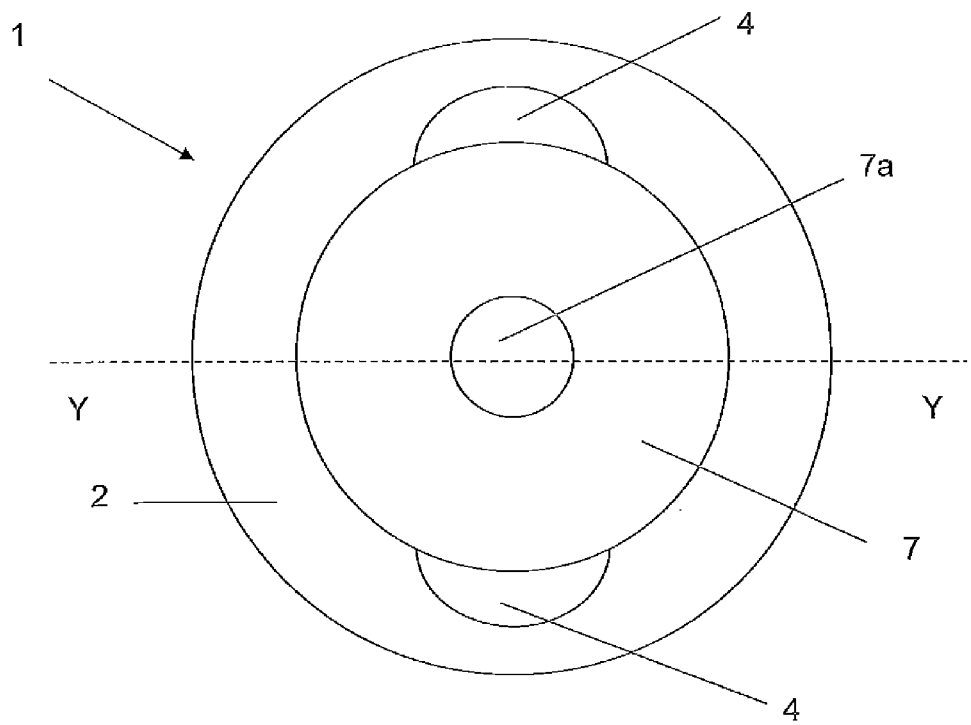
FIG. 1 shows a top perspective, schematic representation of an apparatus for use in grease consistency test in accordance with the present invention.

In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The term "planar" as used herein is intended also to encompass substantially planar configurations.

The term "transparent" as used herein is intended also to encompass substantially transparent materials.

The term "circular" as used herein is intended also to encompass generally circular configurations, including oval configurations.

The term "concentric" as used herein is intended also to encompass generally concentric configurations.

The terms "smooth" and "flat" as used herein are intended also to encompass substantially "smooth" and "flat" configurations.

The steps of each method according an aspect of the present invention will typically be performed sequentially although in some embodiments some of the steps may overlap and be performed concurrently.

A. Grease Characterization Test Kit and Testing Method

The first step comprises applying a volume of a grease to a first surface. The grease may be applied using a spatula or a syringe or the like. In a preferred embodiment, the volume of the grease is known before it is applied. That is, a predetermined volume of grease is applied to the first surface. However, in another embodiment it is possible to determine the volume of the grease after the compression step by calculation and measurement.

Applying a predetermined volume of grease may be achieved by the provision of a frame having a recess or aperture therein defining the desired volume. The recess or aperture is simply filled with the grease and the predetermined volume of grease then transferred to the first substrate. The frame may take the form of a circular disc having a central circular aperture. The volume defined by the circular aperture corresponds to the volume of grease to be applied to the first surface. In an alternative embodiment, a predetermined volume of grease may be applied to the first surface using a syringe.

The volume of grease used is typically from 0.01 ml to 10 ml, preferably from 0.05 ml to 5 ml, more preferably from 0.1 ml to 1 ml.

The first and second surfaces are preferably planar surfaces and are made of a non-absorbent material. The surfaces are also preferably smooth. The use of planar, smooth, non-absorbent surfaces helps to promote even spreading of the grease under compression. It also facilitates cleaning of the testing apparatus and minimizes cross contamination of grease samples.

The surfaces are also preferably inert and do not react with the grease being tested. Preferred materials for the substrates include non-reactive metals and alloys, polymers, ceramics and glasses.

The first surface can be one side of a first substrate, such as a circular disc. The second surface can be one side of a second substrate, being another circular disc. The diameter of the discs is preferably the same. In a preferred embodiment, the frame is also a circular disc having the same diameter as the first and second discs. As noted above, the frame preferably has a central circular aperture, which defines the volume of grease to be applied to the first surface.

The first and second surfaces can also be opposing surfaces of one and the same object.

In one embodiment, it is preferred that at least one of the substrates is transparent. This makes it possible to observe the grease through the transparent substrate. A preferred substrate is therefore formed from a glass or polymer material.

In a particularly preferred embodiment, both the first and second substrates are transparent. The scale used for determining the grease consistency can then be arranged beneath the substrates to determine the extent that the grease has spread under compression.

In another embodiment, one of the first and second substrates is transparent. The scale is then arranged on one of the first and second substrates so as to be visible when the grease is visible. For example, the scale may be provided on the first surface and be visible through a transparent second substrate. Alternatively, the second substrate may be transparent with visible markings provided on the surface in contact with the grease, i.e. on the second surface, or provided within the second substrate or on the surface of the second substrate distal from the grease.

The first step of the method according to the present invention further comprises arranging a second surface in contact with the grease, distal from the first surface, and then applying a compressive force to the first and second surfaces such that the grease is caused to spread therebetween. The compressive force is applied for a predetermined period of time. In one embodiment, the predetermined period of time is an amount of time sufficient for the predetermined volume of grease to stop or substantially stop spreading under compression. In another embodiment, the method comprises measuring the predetermined period of time and applying the compressive force for this time, regardless of whether the grease has ceased to spread under compression.

Preferably, the first and second surfaces are arranged to lie substantially parallel to each other. The compressive force can be applied by placing a mass on top of the second substrate that comprises the second surface. Alternatively, the second surface can be an underside of the mass. A mechanical clamp could also be used to compress the first and second surfaces.

The second step in the method according to the invention comprises measuring the extent that the grease has spread between the first and second surfaces. The extent as used herein refers to an outline of the compressed volume of grease. Hence, the extent of grease spreading can be seen as the area covered by the compressed grease, the diameter of a circular or substantially circular grease sample, the width of a non-circular regular sample or the furthest point on a line reached by the grease under compression, or a thickness of the compressed grease.

The act of determining the extent of spreading can be performed by directly measuring the extent as defined above or by comparing the extent of spreading against a scale according to the invention.

In the third step of the inventive method, the grease consistency is determined from the measured extent of grease spreading, on the basis of the relationship therewith. As mentioned, this can be done e.g. using a lookup table or a graph that has been calibrated for the volume of grease tested and for the magnitude and duration of the compressive force applied. When a scale according to the invention is used, the consistency of the grease can be determined by observing the furthest marking covered by the compressed grease or the closest marking to the furthest extent of the grease.

In a preferred embodiment, the scale comprises a series of graduated markings. The markings can be sequential linear markings akin to those on a ruler, or a series of concentric outlines. In a preferred embodiment the markings correspond to the external shape of the perimeter of the grease sample before compression. Thus, when the grease is compressed the grease expands equally (or substantially equally) in all directions and the extent of spreading overlaps the markings. It is preferred that the markings are concentric outlines that are preferably circular.

The scale used for determining the consistency is calibrated with respect to the volume of the grease being tested and the magnitude and duration of the force that is applied to compress it. Although the volume of grease tested, the applied compressive force and its duration are in themselves unimportant, the scale needs to be calibrated with respect to these parameters in order to provide useful and reproducible results.

In one embodiment, the scale is calibrated with respect to a specific time period for which the grease is compressed. That is, the grease is compressed for a measured period of time and the extent that the grease covers is then observed. In another embodiment, the scale is calibrated with respect to a period of time during which a predetermined volume of all grease grades stops or substantially stops spreading under the application of a predetermined compressive force. When a grease sample is then tested using the inventive method, the compressive force can be applied until no further discernible increase in the extent of spreading is observed. The predetermined period of time can be from one second (1 s) to five minutes (5 mins), preferably from five seconds (5 s) to one minute (1 min), and most preferably from ten seconds to thirty seconds (30 s).

In an alternative embodiment, it is the time that is recorded. Hence, the time required for a grease to reach a given extent of coverage is recorded. This is a less preferred embodiment since it requires more complicated measurements, although this could, of course, be computer controlled to automate the procedure. In this embodiment, it is preferred that the force is applied in a transparent manner, e.g. pushing on the edges of the transparent substrate(s), air jets or a transparent weight, or any other method known in the art.

In one embodiment, the marking system provides a single mark. If the grease fails to spread beyond the mark or spreads beyond the mark, then the grease is no longer suitable for its purpose. Alternatively two marks can be used to provide a tolerance within which a suitable grease should fall.

In another preferred embodiment, the calibrated scale comprises graduated markings that correspond to the NLGI grease grade system. The markings can correspond to grade values, or partial grade values (for example, halves or quarters) or to the corresponding cone penetration depth on which the grade is based.

In another preferred embodiment, the scale is also calibrated with respect to the temperature at which the testing is conducted. This is advantageous when the grease being tested is extremely sensitive to temperature. When the scale is calibrated with respect to the NLGI grades, a change in testing temperature could provide a mismatched result of the NLGI grade of the tested grease.

In view of the nature of the test, it is preferred that testing is conducted at ambient temperature, typically from 0 to 50° C. More typically, the testing will be conducted at room temperature, from 15 to 30° C. When an extremely accurate correlation with cone penetration depth is required, it is preferred that testing is conducted close to or at the ASTM D217 temperature of 25° C.

The force applied to the first and second surfaces to compress the grease therebetween is preferably provided by using a predetermined mass acted on by gravity. The mass can be rested on one of the substrates in order to compress the grease applied between the substrates. It is of course possible to provide the force though the use of a mechanical system. In this case the suitable amount of force can be determined by using the equivalent forces as is provided by the below masses (i.e. the mass multiplied by 9.81, whereby the mass comprises the weight of the second substrate, when present).

The mass used is typically from 10 g to 1 kg, preferably from 25 g to 750 g, more preferably from 100 g to 400 g and still more preferably from 150 g to 250 g.

The mass may take the form of a circular disc, typically formed from a metal or alloy. In a preferred embodiment, the first substrate, the second substrate, the frame, and the mass are all circular discs having approximately the same diameter. As noted above, the frame preferably has a circular central aperture, which defines the volume of grease to be applied to the first substrate. The volume of grease defined by the aperture and the mass applied to compress this volume are suitably selected such that a grease sample of the stiffest grade spreads by a visibly discernible amount under compression, and such that the extent of spreading exhibited by a grease sample of the softest grade is not greater than the diameter of the frame and circular discs.

The apparatus advantageously further comprises a housing for the first and second surfaces, the frame, and the mass. Where the component parts of the apparatus are provided in the form of same-diameter discs, then the housing advantageously has inner walls defining a cylinder having a diameter that is slightly greater than the diameter of the discs. This configuration ensures that there is little or no horizontal translation of any of the discs during operation of the method according to the present invention, which might affect measurements.

The force required depends on the amount of grease tested. However, as the area over which the force is applied varies over time as the grease spreads, it is not possible to recite desirable pressures. More suitable units are the force applied per unit of grease compressed. Accordingly, it is preferred that the force per ml of grease is from 1N/ml to 100N/ml, more preferably from 10 to 20N/ml.

The apparatus according to the second aspect of the present invention may be used to perform the method as described herein and may be adapted in accordance with any of the method features described above.

According to the third aspect, the present invention provides a calibrated scale configured for use in determining the consistency of a grease, the scale comprising a graduated set of markings that are calibrated to correspond to a cone penetration depths according to ASTM D217 or NLGI grease classification grades. The scale is configured to allow visual determination of the grease consistency by observing the extent of spreading exhibited by a predetermined volume of grease placed centrally to the markings that has been subjected to compression by a predetermined force for a predetermined period of time. The scale is calibrated with respect to the predetermined volume, the predetermined force, the predetermined period of time and preferably also a predetermined temperature or temperature range. In a preferred embodiment the graduated markings are concentric circular markings.

The scale needs to be calibrated. If the volume and force are the same, then a pre-calibrated scale can be used. A scale can be calibrated in the following way. The amount of grease (volume) to be tested is determined. This will depend on e.g. the bearing type and the amount of grease available for testing. A suitable force is selected. If necessary, a suitable force can be determined by selecting a force sufficient to cause a grade 5 grease to spread by a visible and obvious amount. That is by one millimeter (1 mm) or more along a scale or for the outward perimeter of the area that the grease covers to expand by 1 mm (a 0.5 mm increase in radius for a circular marking). A suitable period of time for applying the compressive force is then selected. Preferably, the period of time is sufficient to allow the selected volume of grease to stop spreading under the selected compressive force.

When the test conditions have been selected, the markings can be calibrated by noting the extent of spreading by standard grade greases when they undergo the method of the present invention at the selected test conditions. Alternatively, a cone penetration test according to ASTM D217 can be performed on the greases that have been compressed according to the method of the invention and the markings can be calibrated to a corresponding cone penetration depth.

If it is necessary to calibrate with respect to the test temperature, then the calibration should be done for the desired temperature at which testing will be conducted.

It has been found that the thickness or consistency of a grease, which is normally determined by measuring the penetration of a cone, can be accurately determined by the claimed method. Of particular note is that the relationship between the compression spreading of the grease and the consistency of the grease is essentially linear, when the extent of spreading is measured in one dimension. When surface area is measured, the relationship between compression spreading and greases consistency obeys a square law.

This simple grease test is an important predictive maintenance tool. The test can be performed using simple apparatus that does not require a power supply, and can therefore be executed on-site to quickly direct necessary maintenance. An important advantage of this approach is that the sample does not need be removed to a remote site for testing. Another benefit of the method is that it can provide an actual penetration number, as well as a NLGI grade number. The method can also be used on small sample sizes, which is beneficial for difficult-to-reach grease locations.

Figure 2:
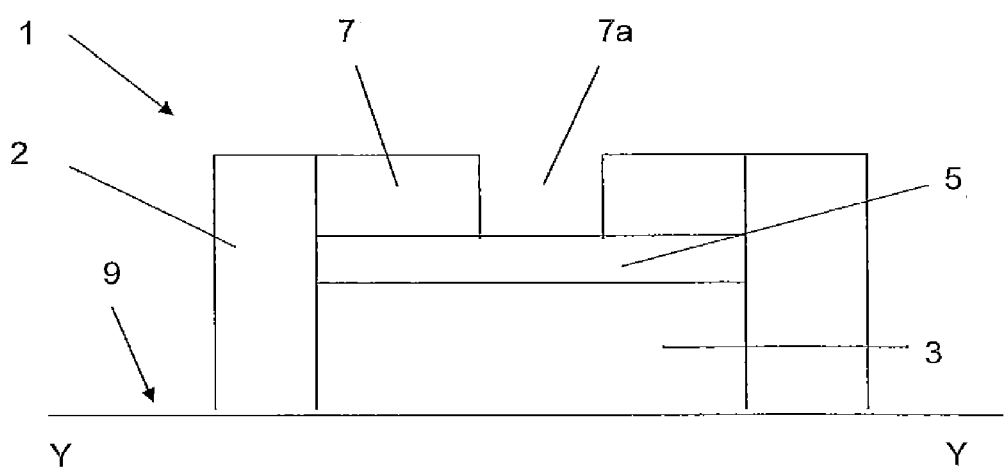
FIG. 2 shows a schematic cross-section of the apparatus taken along the line Y-Y as indicated in FIG. 1.
Figure 3:
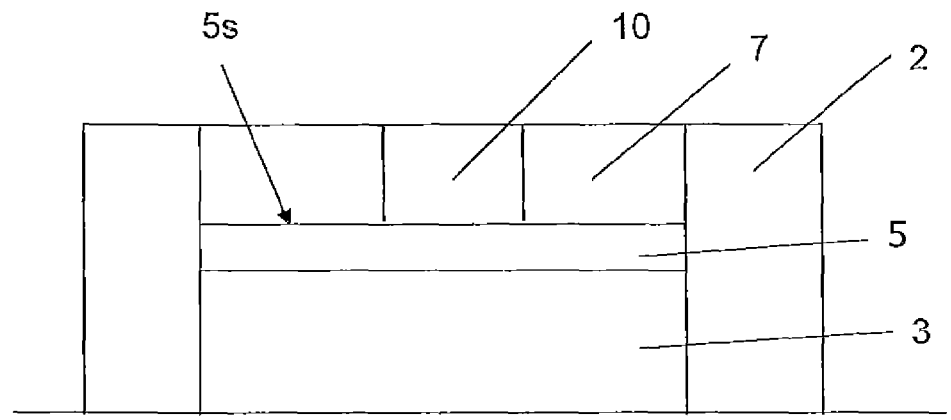
FIG. 3 shows a schematic cross-section of the apparatus arranged after the introduction of a grease sample.
Figure 4:
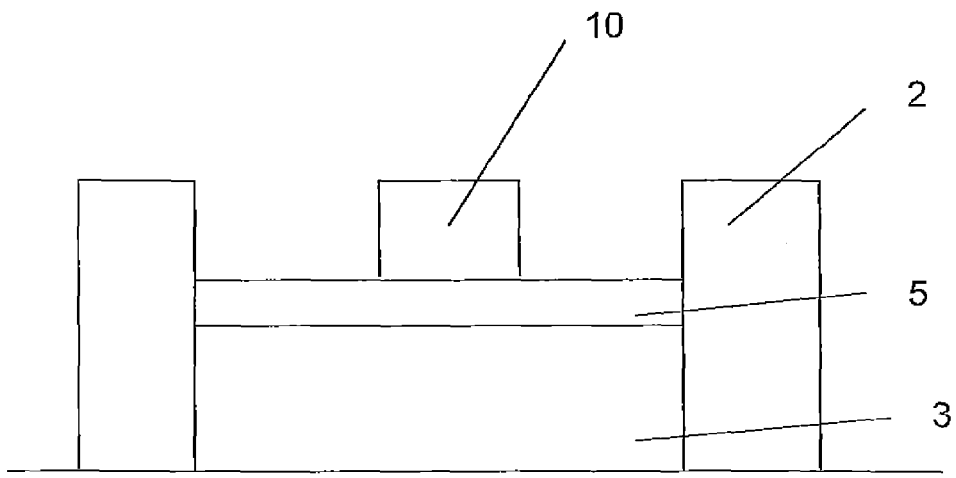
FIG. 4 shows a schematic cross-section of the apparatus arranged once a framing slide has been removed.

Referring now to FIGS. 1-9 in detail, FIGS. 1 and 2 respectively show a top view and a side view of one example of a grease testing apparatus according to the invention, in which the consistency of a grease is determined by compressing a predetermined volume of the grease between two surfaces and measuring an extent to which the grease spreads under compression. In this example, the grease testing apparatus 1 comprises a housing 2 in which a mass 3, a first substrate 5, and a frame 7 are arranged on top of each other. Each component part of the apparatus is a separate part that can be assembled on a base 9, such as a tabletop. The frame 7 has a central aperture 7a, which defines the predetermined volume of grease to be tested. The first substrate 5 has a surface that serves as one of the surfaces between which the grease is compressed and the mass 3 represents a means to apply the compressive force. The mass 3 can also serve as means to facilitate the provision of a predetermined volume on grease on the first substrate 5, as shown in FIGS. 2-4.

The housing 2 can be a cylinder having a cylindrical internal diameter which defines an internal cavity for locating the other component parts of the testing apparatus. Advantageously, the cylindrical internal diameter of the housing 2 can comprise two opposing recessed portions 4 which extend over the full height of the housing, to enable the components located therein to be gripped and removed by hand.

In the depicted embodiment, the first substrate 5, the frame 7, and the mass 3 are all in the form of circular discs having approximately the same diameter, which diameter is slightly less than the diameter of the internal cavity of the housing 2. The first substrate 5 and the mass 3 are solid discs. In contrast, the frame 7 has the central aperture 7a defining a desired volume corresponding to the volume of grease to be tested.

With reference to FIG. 3, the first step in performing a test to determine the consistency of a grease, according to the method of the invention, is to provide a predetermined amount of grease 10 on a surface 5s of the first substrate 5. This may be achieved by stacking within the housing 2 the mass 3, the first substrate 5 and the frame 7, with the frame 7 being uppermost and the first substrate 5 directly below. As shown in FIG. 3, the height of the housing 2 can be approximately the same as the sum of the thicknesses of the first substrate 5, the mass 3 and the frame 7. It is advantageous for the frame 7 to be held at least partially within the housing 2, since this prevents translational movement when a grease sample is introduced into the central aperture. Thus, the mass 3 initially serves as a flat support for the first substrate 5 and the frame 7, to position these components at a suitable height within the housing to enable the grease sample 10 to be provided as described.

Advantageously, the sample of grease to be tested is worked before its consistency is determined. For example, the grease sample may be stirred for 10-30 seconds prior to testing. This is particularly beneficial when the grease to be tested is an old or used grease. A skin can develop on old and used greases, which might interfere with the consistency determination by causing the grease to spread unevenly when subjected to compression in the method according to the invention. The stirring homogenizes the consistency of the grease and therefore improves the reliability of the test results.

The grease sample is deposited onto the surface 5s of the first substrate 5 in an amount sufficient to fill the central aperture in the frame 7. Any excess grease can be removed by wiping the upper surface of the frame 7 with a spatula or the like. Thus, the surface of the grease sample 10 is smoothed to make it level with the uppermost surface of the frame 7.

The frame 7 is then removed by lifting it out of the housing 2, thereby leaving a free-standing, grease sample 10 of predetermined volume on the top surface 5s of the first substrate 5, as shown in FIG. 4.

Figure 5:
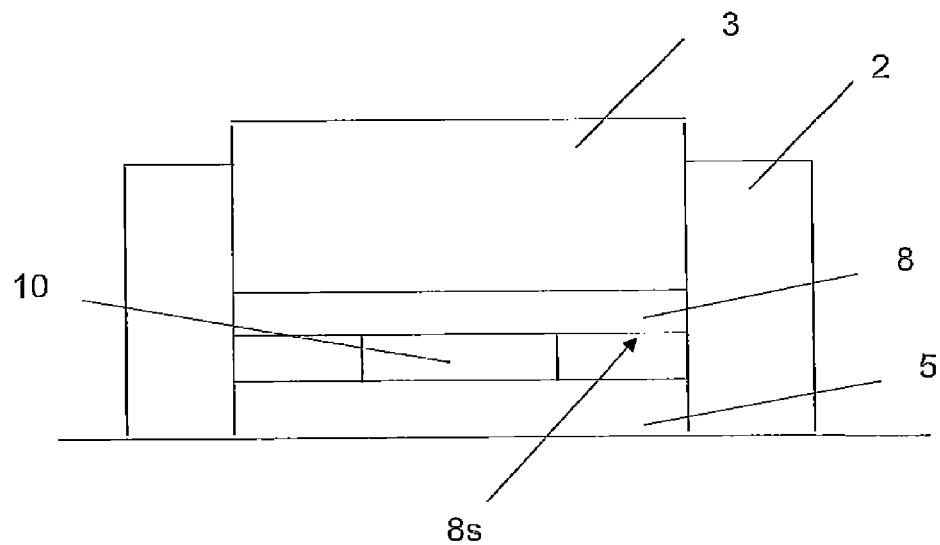
FIG. 5 shows a schematic cross-section of the apparatus in use, whereby a grease sample is being compressed.

Next, the first substrate 5 comprising the grease sample 10 and the mass 3 are lifted out of the housing and rearranged to correspond to the configuration shown in FIG. 5, so that the mass 3 may be used to compress the grease sample. The dual purpose of the mass 3—as a support for the first substrate 5 and the frame 7 and as a means for applying the compressive force—reduces the number of components in this example of a test apparatus according to the invention, but, as will be readily understood, separate components may be used.

With reference to FIG. 4, the first substrate 5 is reintroduced into the cavity of the housing 2 as the lowermost part. Then, a second substrate 8 is carefully lowered into the housing 2 so that it rests on top of the grease sample 10. The second substrate 8 can be identical to the first substrate 5, i.e. a solid disc with a diameter only slightly less than the internal diameter of the cylindrical housing 2. The second substrate 8 has a surface 8s that is placed in contact with the grease.

The mass 3 is then carefully lowered into the housing 2 so that it rests on top of the second substrate 8 and causes the grease sample 10 to be compressed between the surfaces 5s, 8s of the first and second substrates 5, 8. Owing to the shape and configuration of the first substrate 5, the second substrate 8, the mass 3, and the cylindrical cavity of the housing 2, the second substrate 8 is forced to descend substantially parallel to a central axis of the cylindrical cavity of the housing 2. This prevents any sheer force being applied to the grease sample 10 by any movement perpendicular to the central axis of the housing cavity. In other words, the wall defining the cylindrical cavity of the housing 2 acts as a guide for the other components of the apparatus.

The mass 3 is left in place for a period of time before being removed from the housing 2. The period of time is preferably predetermined and may be measured with a timing mechanism, such as a stop-watch.

Figure 6:
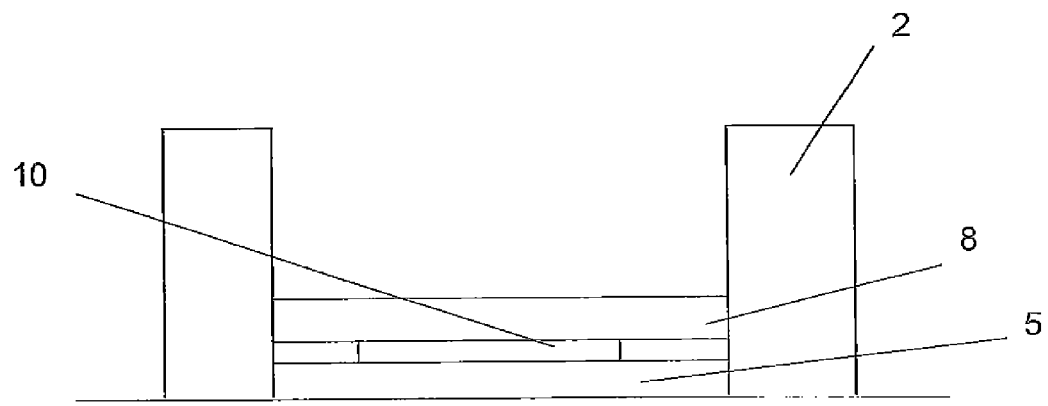
FIG. 6 shows a schematic cross-section of the apparatus, after compression of the grease sample.

FIG. 6 shows the apparatus once the mass 3 has been removed. The grease sample 10 has been compressed between the first substrate 5 and the second substrate 8. In other words, the grease sample has spread and its diameter has increased relative to its starting diameter. According to the method of the invention, the increase in the diameter of the grease sample 10 can be directly correlated to an international grease classification standard.

Figures 7A, 7B:
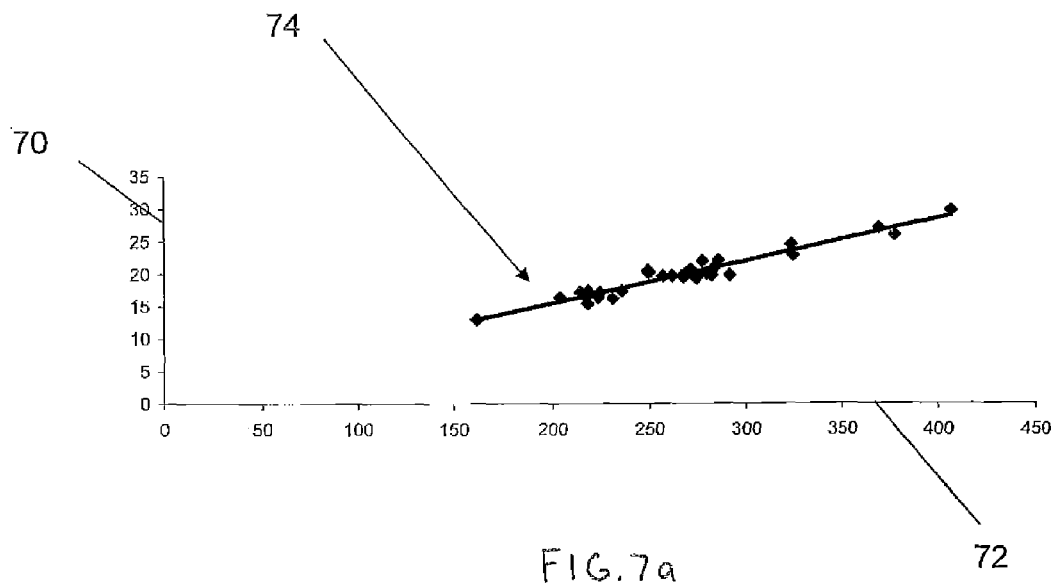
FIG. 7a shows a plot of the diameter of compressed grease samples against corresponding cone penetration depth.
FIG. 7b shows a table of NLGI grades and corresponding cone penetration depths.

An example of the correlation is illustrated in the graph of FIG. 7a, which shows a plot of the results obtained from testing the consistency of different greases by means of:

(i.) the method of the invention, in which the diameter of each grease sample was measured after a predetermined volume of the grease had been subjected to a predetermined compressive force for a predetermined time;

(ii.) a cone penetration test in accordance with ASTM D217.

The ordinate 70 in the graph of FIG. 7a represents measured diameter (in mm) after grease compression, while the abscissa 72 represents cone penetration depth (in 0.1 mm) As shown, a straight line 74 can be drawn though the data points, indicating a linear correlation between the extent to which a predetermined volume of grease spreads under compression and the depth to which a standardized cone penetrates the same grease.

NLGI grade is an internationally recognized classification standard for classifying lubricating greases according to their consistency. The relationship between NLGI grade and cone penetration depth is shown in the table of FIG. 7b, whereby grade "000" represents the softest grease consistency and grade "6" represents the stiffest grease consistency. The penetration depths in the graph of FIG. 7a can therefore be expressed in terms of NLGI grade, so that the consistency grade may be obtained directly from the graph. Due to the linear relationship between grease diameter increase under compression and NLGI grade (cone penetration depth), half NLGI grades can also be determined.

In one embodiment of the method according to the invention, the diameter of a compressed grease sample is simply measured and the grease consistency is obtained by comparing the measured diameter with a suitably calibrated graph of the type shown in FIG. 7a. Calibrated look-up tables can also be used. As will be understood, calibration is necessary because the actual diameter of a compressed grease sample will differ depending on the volume of the grease sample and the magnitude of the compressive force applied. The duration of the applied force is also a factor. Preferably, the graph or lookup table is calibrated on the basis of a compressive force duration that is sufficient for the grease sample to stop spreading under compression. This duration may therefore be exceeded without affecting the grease consistency determination. The compressive force may also be applied for a predetermined period of time that is insufficient for the grease to stop spreading, in which case the graph or lookup table must be calibrated for this predetermined period of time.

Figure 8:
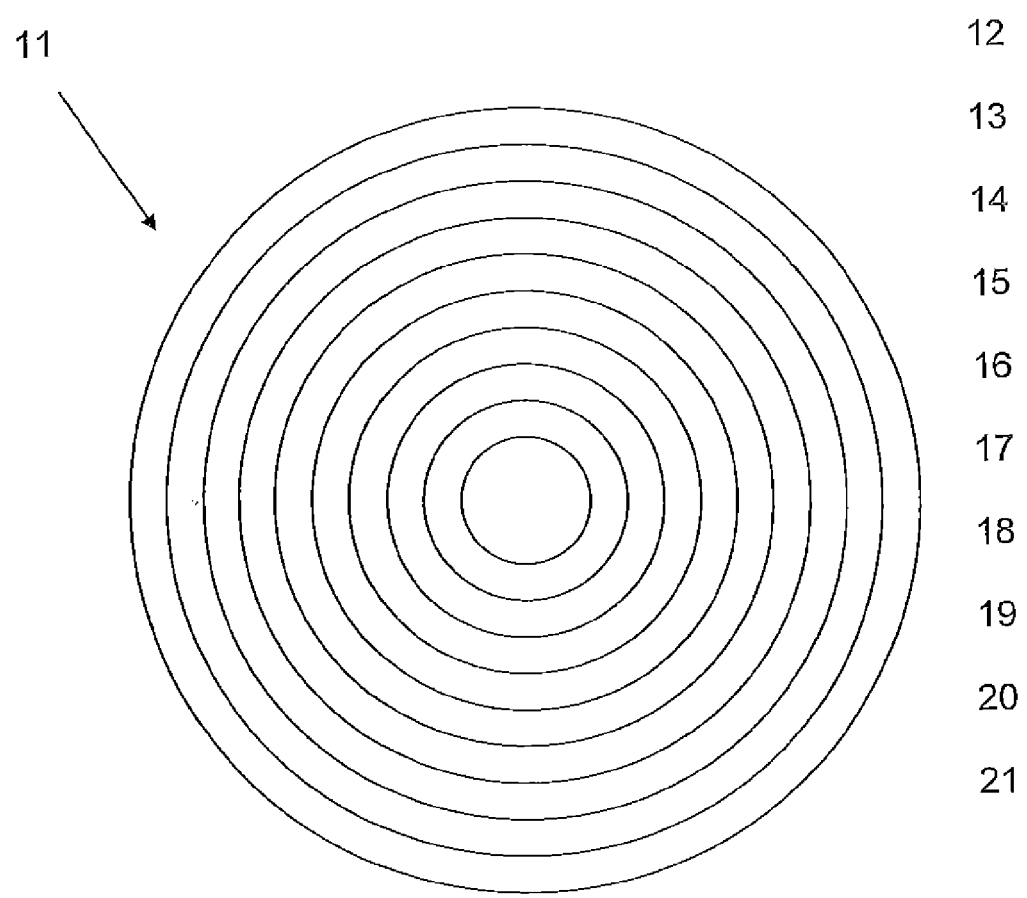
FIG. 8 shows an exemplary diagram of an NLGI calibrated scale for determining the consistency of a grease.

In a preferred embodiment, the correlation between grease spreading and NLGI grade is applied to create a visual scale, which scale can be used in combination with an apparatus according to the invention. An example of a suitable scale is shown in FIG. 8.

The scale 11 comprises a series of circular, concentric markings. In this example, an innermost circular marking 12 has the same radius as the circular aperture in the frame for obtaining the predetermined volume of grease. A next concentric marking 13, lying immediately outward of the innermost marking 12, corresponds to a NLGI grade of "6". Thereafter, the consecutively outward circular markings 14, 15, 16, 17, 18, 19, 20, 21 respectively correspond to NLGI grades of "5", "4", "3", "2", "1", "0", "00" and "000". Because each NLGI grade comprises a small range of grease consistencies, the concentric markings 13, 14, 15, 16, 17, 18, 19, 20 and 21 in FIG. 8 indicate a lower limit for the corresponding NLGI grade.

In some embodiments, the scale also comprises markings that correspond to half numbers of NLGI grade. Each region between two consecutive markings may be given a different color, such that each NLGI grade is recognizable from its color coding. In other embodiments, the concentric markings on the scale correspond to cone penetration depths according to ASTM D217. The scale 11 can also advantageously comprise an outermost circular marking (not shown) with a diameter equal to the diameter of the housing 2, to enable the apparatus 1 to be correctly positioned such that the centre of the scale 11 coincides with the centre of the grease sample.

Figure 9:
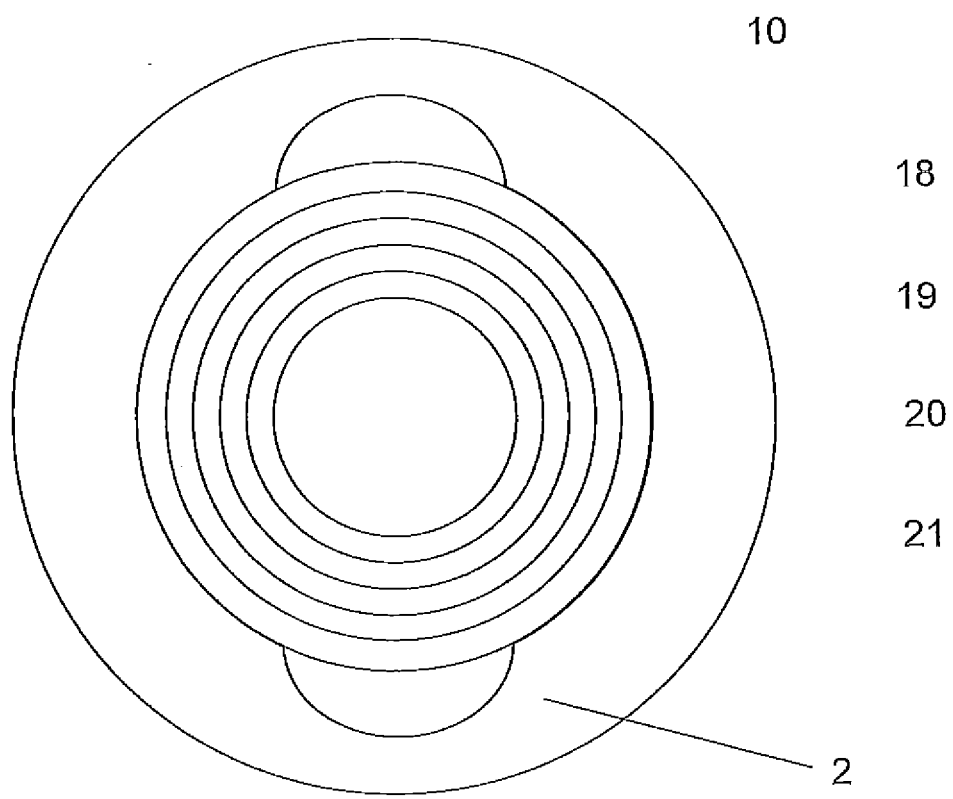
FIG. 9 shows a schematic view from above of the apparatus used in combination with a scale of the type shown in FIG. 8.

FIG. 9 shows a top view of the apparatus as shown in FIG. 7, whereby the apparatus 1 has been arranged on a scale according to the invention and the first and second substrates are made of a transparent material. The scale is calibrated with respect to the volume of the grease sample 10 and the magnitude and duration of the compressive force applied thereto. The compressed grease sample 10 is visible through the transparent second substrate. Concentric markings 18, 19, 20, 21 of the scale are visible through the transparent first and second substrates, whereby the markings 18, 19, 20 and 21 respectively correspond to NLGI grades "1", "0", "00" and "000". Thus, the extent to which the grease has spread under compression can be matched to the nearest-lying concentric marking on the scale and the grease consistency can be immediately identified. If FIG. 9 depicted a real example, a person conducting the grease test would deduce that the furthest extent of the compressed grease sample lies closest to the (hidden) marking that represents a NLGI grade of "2".

The present invention therefore provides a simple and accurate method for determining the consistency of a grease on-site and away from the laboratory.

B. Bleed Characterization Test Kit and Methods

Referring now to FIGS. 10-22, a test kit 100 for testing the oil bleed characteristic of used grease basically comprises at least one and preferably a plurality of pieces of a test medium 102, a heater 104, and a scale 106. The at least one piece of test medium 102 is configured to receive a "sample" quantity $Q_G$ of the used grease so as to form a test sample 101 and the heater 104 is configured to heat the test sample 101. The scale 106 is configured to measure a dimension $D_G$ of the used grease quantity $Q_G$ on the test sample 101 after the sample 101 has been heated. More specifically, when the sample 101 is heated, at least a portion of the oil within the grease quantity $Q_G$ flows or disperses upon the test medium 102, so as to form a bleed zone $Z_B$ about the original boundary of the grease quantity $Q_G$. The dimension $D_G$, which is preferably the average diameter of the bleed zone $Z_B$, is compared with a reference so as to determine a bleed characteristic of the used grease, as described in detail below. Preferably, the bleed characteristic test kit 100 further comprises written instructions 110 for performing the bleed characteristic test, as described below, most preferably included within a test kit manual.

Referring to FIGS. 10 and 13-21, each piece of test medium 102 is preferably a sheet of paper 105, and most preferably a non-glossy, circular sheet of paper having a substantially homogenous grid structure of paper fibers (i.e., a web structure), which may be provided by commercially available "laser printer" paper. More specifically, the presently preferred paper sheets each have a weight of about one hundred sixty grams per square meter (160 gr/m$^2$) and a thickness of about nineteen hundredths of a millimeter (0.19 mm) In particular, it is preferred to avoid glossy paper of a relatively small thickness as both the glossiness and thinness tend to exaggerate the effects of base oil viscosity that distorts the evaluation of the oil bleeding from the grease test quantity $Q_G$ on the test sample 101. Preferably, the test kit 110 is provided with a "stack" of a plurality of the paper sheets 105.

Figure 13:
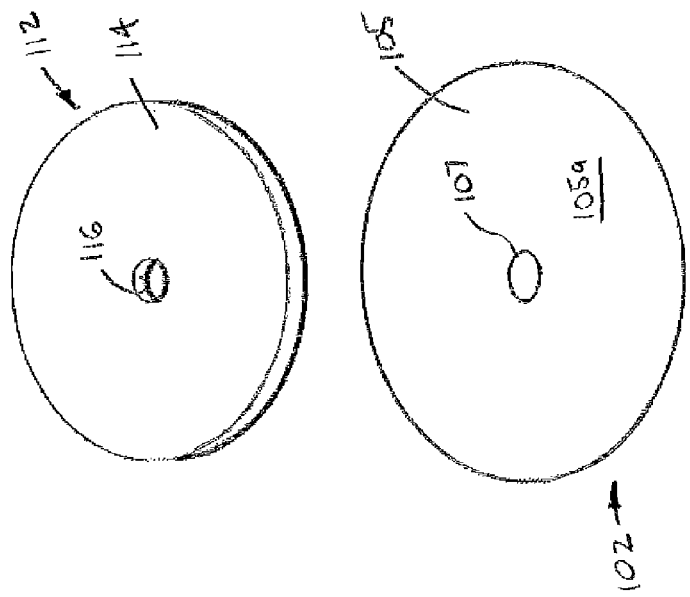
FIG. 13 is an enlarged perspective view of a sample measure and a test medium, shown spaced apart prior to applying grease to form a test sample.

As best shown in FIG. 13, each paper sheet 105 preferably has a sample boundary line 107 formed on at least one surface 105*a* of the sheet 105. The boundary line 107 provides an indication of the initial boundary of the grease quantity QG prior to heating and may be used to meter or provide a predetermined amount/volume of grease when applying the grease quantity $Q_G$ onto the medium 105. Preferably, the boundary line 107 is generally circular, but may have any other appropriate shape. Further, although preferably a sheet of paper 105, the test medium 102 may be provided by any other form of medium capable of receiving a grease sample and being heated such that an oil bleed pattern is formed of the medium 102, for example, a thin plate formed of, or coated with, a substance that enables a capillary-type of flowing or bleeding of the oil.

Figure 10:
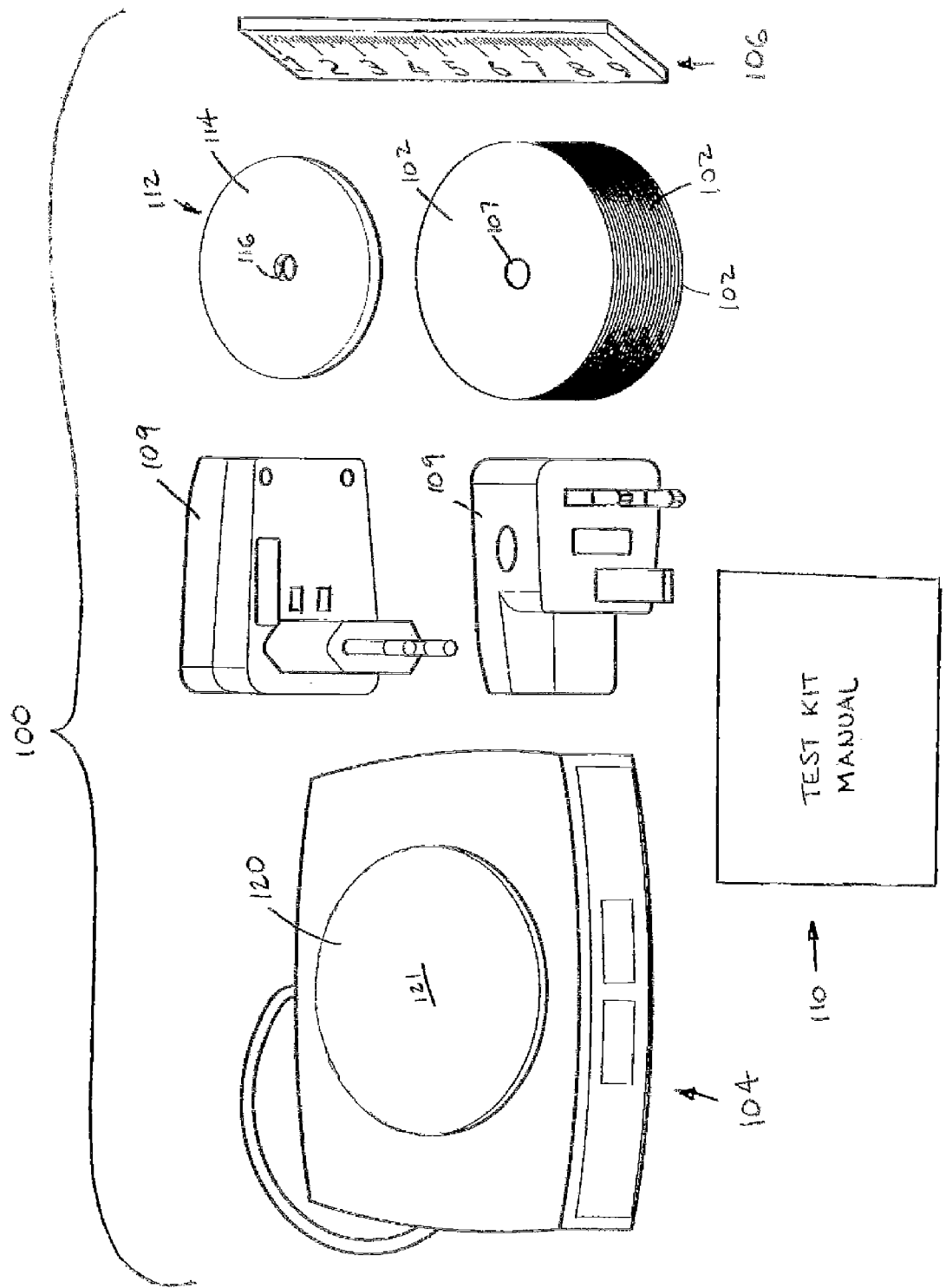
FIG. 10 is a top perspective view of a grease bleed characteristic test kit in accordance with the present invention.
Figure 14:
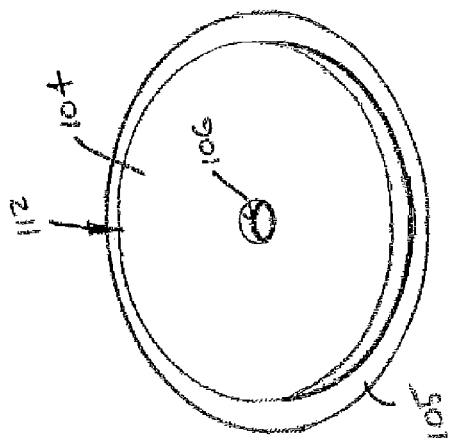
FIG. 14 is a top perspective view of the test measure disposed on a test medium after application of grease.

Referring to FIGS. 10, 13 and 14, the bleed characteristic test kit 100 preferably further comprises a sample measure 112 configured to provide about a predetermined amount of grease on the test medium 102. Preferably, the sample measure includes a plate 114 disposeable upon the test medium 102 and having an opening 116, the opening 116 being sized to meter about the predetermined amount or quantity of grease onto the test medium 102. Thereby, a tester utilizing the kit 100 is able to provide the desired grease quantity $Q_G$ onto the medium 102 by merely filling the opening 104 with grease. Further, the plate opening 114 is preferably generally circular such that the grease quantity $Q_G$ is formed on the test medium 102 in a generally circular pattern. As such, when the test sample 101 is heated, the oil bleed pattern formed on the medium 102 will be generally circular, for reasons described below.

Figure 11:
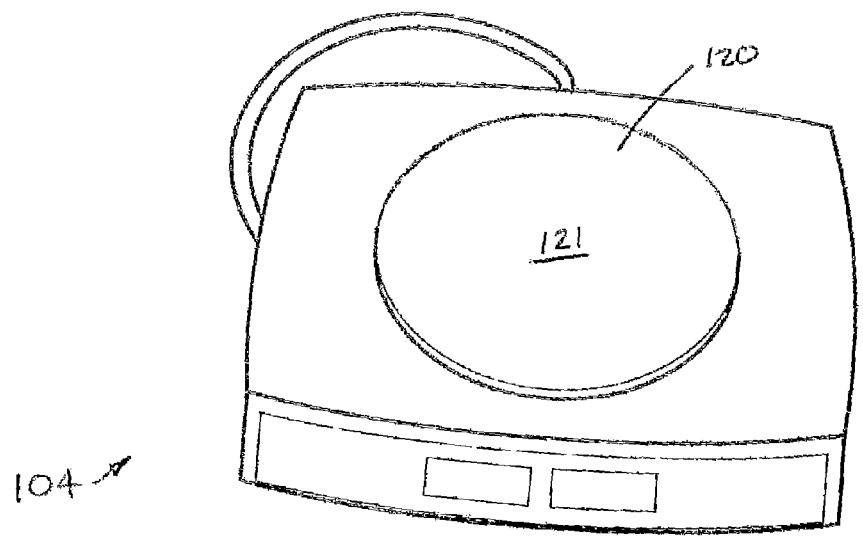
FIG. 11 is an enlarged top perspective view of a preferred heater of the bleed characteristic test kit.
Figure 16:
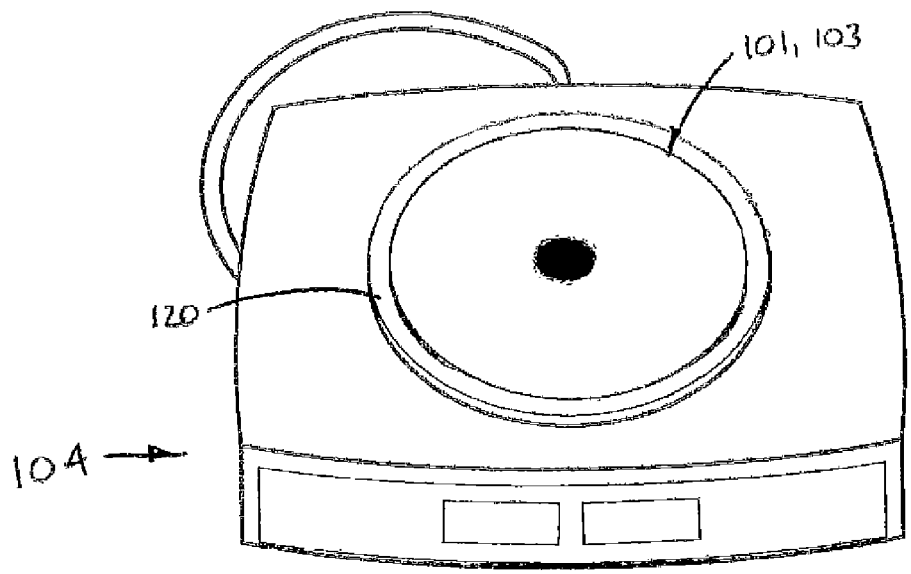
FIG. 16 is a top perspective view of a test sample on the heater at the beginning of the sample heating process.

As best shown in FIGS. 10, 11 and 16, the heater 104 is preferably a "hot plate" type of heater that includes a heater plate 120 with a surface 121 sized to receive the test sample 101 and an electric heating element (not shown), such as one or more resistors, configured to transfer thermal energy to the heater plate such that the plate 120 conducts heat from the surface 121 to the test sample 101. By providing a heater 104 to heat the test sample 101, the rate of oil bleeding on the sample 101 is greatly increased in comparison with a rate of bleeding at room temperature, which could take several days. Although preferably an electric plate type of heater, the heater 104 may be any other appropriate type of heater capable of heating a test medium 102 containing the grease test quantity $Q_G$.

Figure 12:
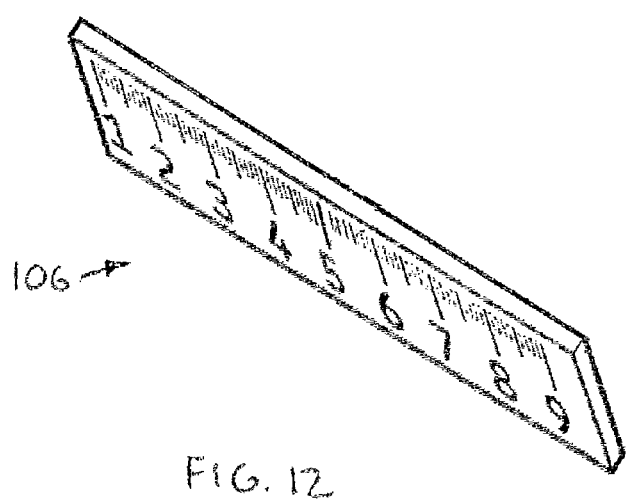
FIG. 12 is an enlarged perspective view of a preferred scale of the bleed characteristic test kit.

Referring to FIGS. 10 and 12, the scale 106 is preferably a standard "ruler" type of measuring device configured to measure distances. Specifically, the scale 106 is configured to measure the diameter of the bleed zone $Z_B$ on the test sample 101, which is preferably measured or "taken" at several locations about the outer circumference of the zone $Z_B$. Although preferably a standard or conventional ruler type of scale, the scale 106 may be a specially manufactured ruler, calipers, etc, or any other type of measuring device capable of measuring or determining the size of the oil bleed zone $Z_B$.

Referring specifically to FIG. 10, the oil bleed characteristic test kit 110 preferably further includes one or more adapters 109 configured to enable the heater 104 to be plugged into electrical power sources in different locations about the world. Further, the test kit 110 also preferably includes a carry case 130 configured to receive all the components of the oil bleed characterization test kit 100 and the apparatus for performing the oil consistency test, as described in detail above. Most preferably, the case 130 includes the equipment necessary to perform these two and other grease testing methods so as to provide a comprehensive grease testing kit 200.

Referring now to FIGS. 13-21, with the items of the test kit 100 as described above, a method for determining the bleed characteristic of used grease basically comprises the following steps: forming a test sample 101 by placing a quantity $Q_G$ of the used grease on a test medium 102, heating the test sample 101, measuring a dimension $D_G$ of the grease quantity $Q_G$ after the sample 101 has been heated, and determining the bleed characteristic of the used grease by comparing the dimension $D_G$ of the used grease with a reference. Preferably, the reference is a measured dimension $D_R$ of a sample or quantity of unused grease, the amount of grease in both the used and unused grease samples being substantially similar. As such, the determination of the bleed characteristic involves determining or calculating the difference between the measured dimension $D_G$ of the used grease and the dimension $D_R$ of the unused grease sample, as described in greater detail below. However, the measured dimension $D_G$ of the used grease sample may be compared with any other appropriate reference, such as a chart of predetermined values for a particular application or grease type.

Figure 15:
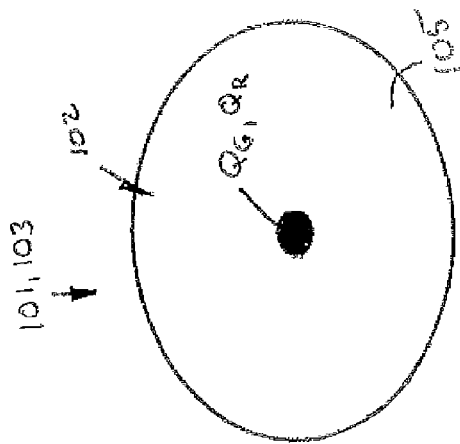
FIG. 15 is a top perspective view of a test sample prior to heating.
Figure 17:
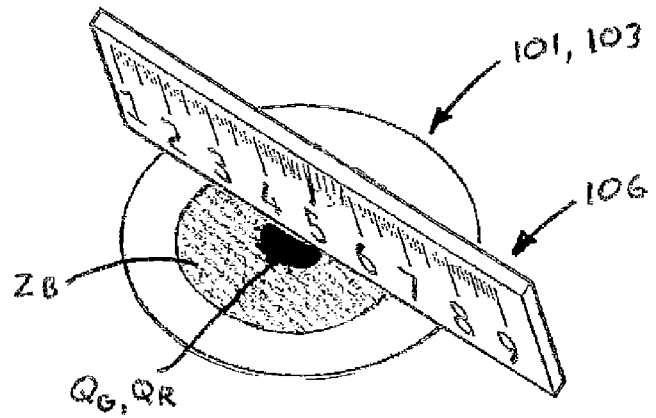
FIG. 17 is a top perspective view of a test sample after heating, showing the scale measuring a dimension of the sample.
Figure 19:
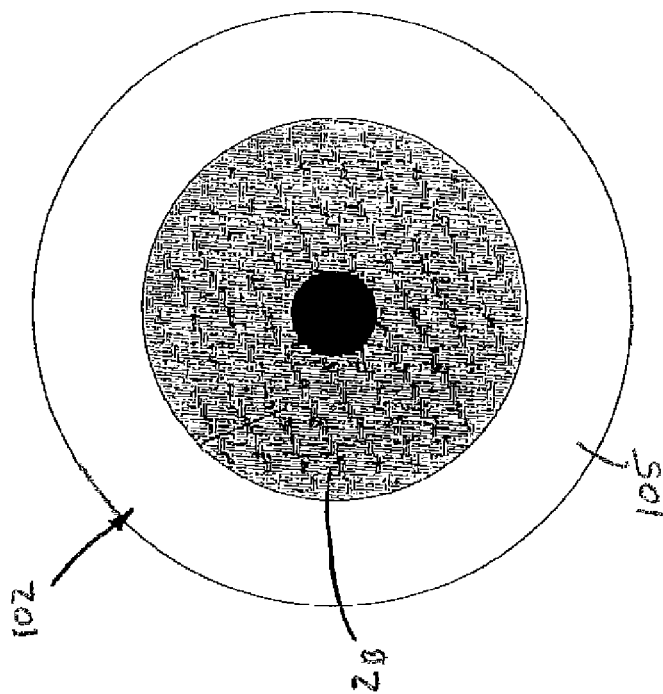
FIG. 19 is a top plan view of a test sample after heating.
Figure 18:
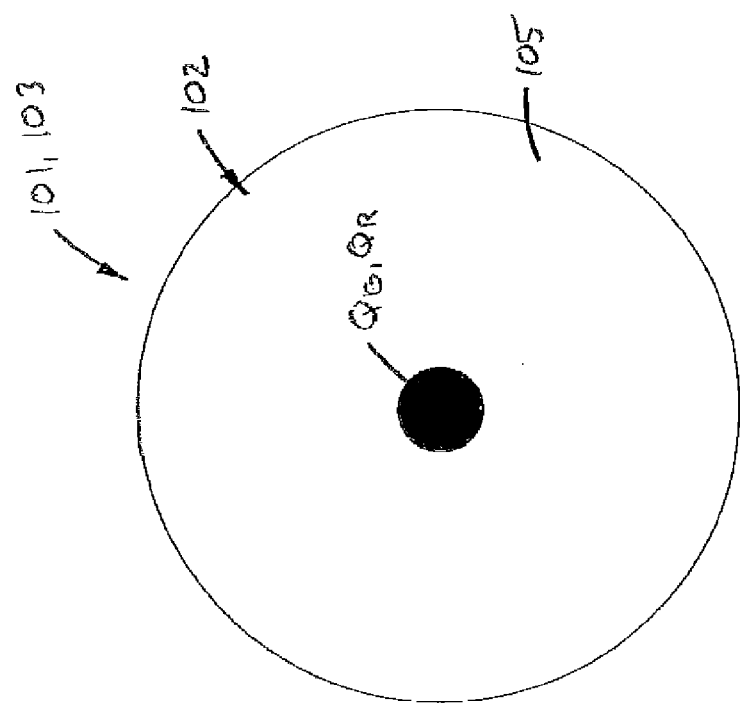
FIG. 18 is a top plan view of a test sample prior to heating.
Figure 22:
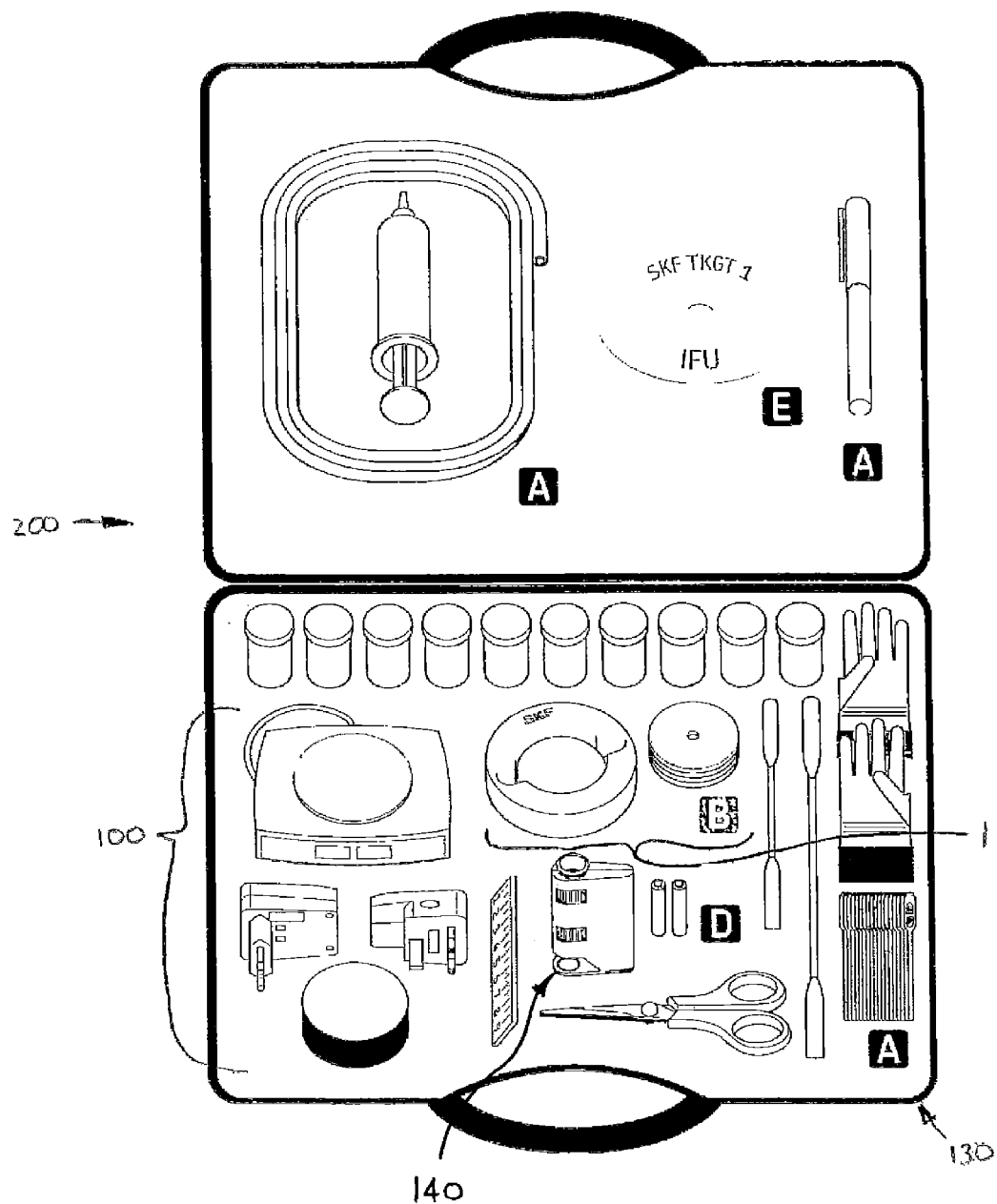
FIG. 22 is a top plan view of an expanded test kit that includes all components necessary to perform all grease tests discussed in this specification or the attached appendix, which is incorporated herein.

Referring to FIGS. 13-15, the method of determining bleed characteristic of used grease preferably involves preparing both a test sample 101 of a quantity $Q_G$ of the used grease and a reference sample 103 of a quantity $Q_R$ of the unused grease. Each sample 101, 103 is prepared in substantially the same manner, preferably by placing the sample measure 112 on a sheet of test paper 105 and then filling the plate opening 116 with either the used grease or the unused grease. Each sample 101, 103 is separately placed on the heater 104 and heated to about a predetermined temperature for a predetermined period of time, preferably to within a range of about sixty degree Celsius (60° C.) to about sixty-five degree Celsius (65° C.) for at least two hours. After each sample 101, 103 has been prepared, each sample 101, 103 is measured as indicated in FIG. 17, preferably by using the scale 106 to measure the diameter of the bleed zone $Z_B$ and most preferably by averaging at least two measurements taken at the largest and smallest diameters of the bleed zone, if the oil bleeding has resulted in a relatively uneven or non-circular pattern. More specifically, approximate minimum dimensions and approximate maximum dimensions (i.e., as determined by visual inspection and judgment of the user) are measured for each of the samples 101, 103 (described below). Then, an average sample bleed zone dimension and an average reference bleed zone dimension are calculated from the measured minimum and maximum dimensions.

Once the test sample and the reference sample have been prepared and measured, the differences between the test sample bleed zone dimension $D_G$ and the reference bleed zone dimension $D_R$ may be compared to determine the oil bleed characteristic of the used grease. Preferably, the circular area of each of the test and reference samples 101, 103 are calculated and compared to determine the difference in the areas of the two samples 101, 103, most preferably expressed as a percentage of the difference between the reference sample bleed zone area and the test sample bleed zone area divided by the reference sample area.

Basically, when the test sample bleed zone dimension $D_R$ or circular area (not indicated) is greater than the reference bleed zone dimension or circular area, as depicted in FIG. 20, an increased oil bleed characteristic of the used grease is indicated, which may be the result of intensive shearing or vibration preventing base oil from remaining in the grease, oil contamination from neighboring devices or systems, a mix of greases or grease with poor mechanical stability. Conversely, when the test sample bleed zone dimension $D_G$ is lesser than the reference bleed zone dimension $D_R$, as shown in FIG. 21, an decreased oil bleed characteristic of the used grease is indicated, which may be caused by loss of base oil, elevated temperature causing base oil oxidation leading to an increase in base oil viscosity, hard particles or a mix of greases.

C. Contamination Test Kit and Methods

Ideally, grease used to lubricate machine components, such as bearings, should free of contaminants as contaminated grease will reduce performance and lifetime of such components. Contamination may come from external sources, such as for example, introduced by poor sealing, dirty grease guns, poor bearing mounting methods, neighboring components, and may be in the form of sand, water, dust, fibers, steam flow, etc. Contamination can also be introduced "internally"; that is, contamination may occur when grease reaches the end of its useful life, such contamination occurring as carbonized particles that formed in the grease, which adhere to surfaces and promote friction.

In any case, it is desirable to determine the extent of contamination, if any, within a sample of used grease. The basic steps of the contamination test are as follows:

1) Visually inspect used grease sample to determine size, amount, shape and nature of those contaminants. Such indication provides an indication on the proper functioning of the bearing or other machine component; and 2) After the consistency test has been performed as described above, the grease sample spread between the two substrates 5 and 8 (e.g., glass plates) can be further inspected using a microscope, as described below More specifically, after the consistency test has been performed, the grease sample disposed between the first and second substrates 5, 7, respectively, is inserted back into the housing 2 of the grease testing apparatus 1. The mass 3 is again lowered into the housing 2 so as to rest on the second substrate, and is then pressed downwardly to displace the second substrate toward the first substrate 3, thereby further "spreading" the sample between the substrates 5, 7 until the sample becomes very thin, preferably about one hundred (100) micrometers.

Thereafter, a user should first visually inspect the sample "with naked eyes", i.e., without aid of any optical magnifying device, to examine the sample for particles, non homogeneity, transparency differences, grit, lumps, or other anomalies. If a reference sample is available, the user should compare both samples. Then, the sample between the substrates 5, 7 should be inserted into a microscope 140 (FIG. 22) and observed to detect the following phenomena. If a glittering of particles is present in the sample, such glittering may indicate that contaminant particles are metallic. As observation of contaminant particles in different positions may be useful, a user can rotate the particles, preferably by pressing the microscope 140 against one of the substrates 5 or 7 plates while rotating the microscope 140. Such rotational movement of the microscope 140 will rotate the substrate 5 or 7 in contact with the microscope 140 to rotate while the other substrate 7, 5 remains stationary or static. A shearing motion is created within the grease sample making particles move and rotate.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as generally defined herein, the appended provisional claims and the attached appendix.

We claim:

1. A method for determining a consistency of a grease, the method comprising the steps of:
   placing a weight mass in a housing with a first surface, a frame having a central aperture to receive predetermined volume of grease to be tested;
   removing the frame after the grease is placed through the central aperture on the first surface,
   placing a second surface on top of the grease and compressing by the weight mass the grease located between the first surface and the second surface positioned and centered in the housing and movable relative the housing, by applying a compressive force by the weight mass to the first surface and the second surface for a period of time, such that the grease is caused to spread between the first surface and the second surface,
   measuring an extent that the grease has spread under compression,
   determining the consistency of the grease from the measured extent of grease spreading on the basis of a relationship therewith, the relationship being calibrated with respect to:
   the volume of grease compressed;
   the compressive force applied; and
   the period of time that the compressive force is applied.

2. A method according to claim 1, wherein the relationship used in the step of determining is further calibrated with respect to a predetermined temperature range.

3. A method according to claim 1, wherein the method comprises a step of measuring ambient temperature or measuring grease temperature and wherein the relationship used in the step of determining grease consistency is further calibrated with respect to the measured temperature.

4. A method according to claim 1, wherein the grease consistency determined corresponds to a cone penetration depth.

5. A method according to claim 1, wherein the step of measuring the extent of grease spreading comprises measuring a surface area covered by the compressed volume of grease.

6. A method according to claim 1, wherein the step of measuring the extent of grease spreading comprises measuring one dimension covered by the compressed volume of grease.

7. A method according to claim 1, wherein the step of determining grease consistency is performed by comparing the extent of spreading to graduated markings of a scale, the graduated markings corresponding to a measure of grease consistency.

8. A method according to claim 7, wherein the scale used is a calibrated scale for determining the consistency of a grease, the scale comprising a graduated set of concentric, circular markings, the scale configured to allow visual determination of the consistency of the grease by observing the extent of spreading exhibited by a predetermined volume of grease placed centrally to the markings that has been subjected to compression by a predetermined force for a predetermined period of time.

9. A method according to claim 7, wherein the scale used to determine grease consistency is calibrated to correspond to the NLGI grease classification.

10. A method according to claim 1, wherein the step of compression is performed using surfaces which are planar and non-absorbent.

11. A method according to claim 1, wherein the force applied to compress the grease between the two surfaces is provided by a mass acted on by gravity.

12. A method according to acclaim 1, wherein the compressive force applied per unit volume of grease is between 1 N/ml and 100 N/ml.

13. A grease testing apparatus comprising:
a housing, a weight mass in the housing with a first surface, a second surface, a frame having a central aperture to receive predetermined volume of grease to be tested;
means for applying a predetermined volume of grease to the first surface and removing the frame after the grease is placed through the central aperture on the first surface;
means for placing the second surface on top of the grease and compressing by the weight mass the grease located between the first surface and the second surface positioned and entered in the housing and movable relative the housing,
means for applying a compressive force by the weight mass to the first surface and the second surface for a period of time, such that the grease is caused to spread between the first surface and the second surface,
means for measuring an extent to which the grease has spread under compression;
means for determining the consistency of the grease using a relationship between grease consistency and the extent of spreading under compression, the relationship being calibrated with respect to:
the volume of grease compressed;
the compressive force applied;
the period of time that the force is applied; and
a predetermined temperature or temperature range.

14. An apparatus according to claim 13, wherein the means for determining grease consistency comprises a scale that is based on the relationship between grease consistency and the extent of spreading, whereby the scale is configured so that, in use, the consistency of a grease is determined by comparing the extent that the grease has spread relative to graduated markings of the scale, the graduating markings corresponding to a measure of grease consistency.

15. An apparatus according to claim 14, wherein the scale comprises a graduated set of concentric, circular markings that correspond to NLGI grease classification grades.

16. An apparatus according to claim 15, wherein the means for applying a compressive force is a mass acted on by gravity.

17. An apparatus according to claim 16 including a calibrated scale for use in determining the consistency of a grease, the seal comprising:
a graduated set of markings that are calibrated to correspond to the NLGI grease classification grades, the scale configured to allow visual determination of the NLGI grade of the grease by observing the extent of spreading exhibited by a predetermined volume of grease placed centrally to the markings that has been subjected to compression by a predetermined force for a predetermined period of time, wherein the scale is calibrate with respect to:
the predetermined volume;
the predetermined force;
the predetermined period of time; and
a predetermined temperature or temperature range.

* * * * *